United States Patent [19]  [11] 4,097,518
Umemura et al.  [45] Jun. 27, 1978

[54] METHOD FOR THE CATALYTIC PRODUCTION OF ACRYLONITRILE

[75] Inventors: Sumio Umemura; Kyoji Ohdan; Taizo Uda; Tokuo Matsuzaki; Mikio Hidaka; Yasuo Nakamura; Tsuruoka, Masao, all of Ube, Japan

[73] Assignee: Produits Chimiques Ugine Kuhlmann, Paris, France

[21] Appl. No.: 733,771

[22] Filed: Oct. 19, 1976

[51] Int. Cl.² ............................................. C07C 120/14
[52] U.S. Cl. .................................. 260/465.3; 252/457; 252/458; 252/467; 252/468; 252/469; 252/470
[58] Field of Search ..................................... 260/465.3

[56] References Cited

U.S. PATENT DOCUMENTS

| | | | |
|---|---|---|---|
| 3,135,783 | 6/1964 | Sennewald et al. | 260/465.3 |
| 3,254,110 | 5/1966 | Sennewald et al. | 260/465.3 |
| 3,342,849 | 9/1967 | Brill et al. | 260/465.3 |
| 3,424,782 | 1/1969 | Ohmori et al. | 260/465.3 |
| 3,642,930 | 2/1972 | Grasselli et al. | 260/465.3 X |
| 3,883,573 | 5/1975 | Milberger et al. | 260/465.3 |
| 3,907,713 | 9/1975 | Grasselli et al. | 260/465.3 |
| 3,907,859 | 9/1975 | Grasselli et al. | 260/465.3 |
| 3,911,089 | 10/1975 | Shiraishi et al. | 260/465.3 |

*Primary Examiner*—Joseph Paul Brust
*Attorney, Agent, or Firm*—Brooks, Haidt, Haffner & Delahunty

[57] ABSTRACT

High-yield catalytic production of acrylonitrile at an elevated temperature, from a reaction mixture containing propylene, ammonia and molecular oxygen, utilizing a catalyst comprising an oxide composition having the empirical formula $Mo_aCo_bFe_cX_dO_e$ wherein X denotes at least one atom of an element selected from among calcium, tungsten, chromium, zirconium, titanium, zinc, manganese, and tin and the atomic ratio $a:b:c:d:e$ is in the range of 12:4 to 10:1 to 6:0 to 1.0:40 to 70, said catalyst being prepared by providing an aqueous mixture containing compounds of the elements, drying the aqueous mixture, and calcining the dried solid product at a temperature of at least 500° C.

18 Claims, No Drawings

METHOD FOR THE CATALYTIC PRODUCTION OF ACRYLONITRILE

BACKGROUND OF THE INVENTION

The present invention relates to a method for the production of acrylonitrile, and more particularly, it relates to a method for the production of acrylonitrile by a catalytic ammoxidation of propylene in the gas phase at an elevated temperature in the presence of a catalyst containing no bismuth.

Various methods are well-known for the production of acrylonitrile by contacting propylene with molecular oxygen and ammonia in gas phase in the presence of a catalyst at an elevated temperature. Various types of catalysts are also provided for the above methods. The conventional types of catalysts consist mostly of oxide compositions which contain combinations of oxides of a plurality of elements. A large number of the conventional catalysts contain bismuth and molybdenum as catalytic ingredient elements. For example, Japanese patent application publication No. 36-5870 (1961) discloses an Mo—Bi—(P)—O catalyst, and Japanese Patent Application Publication No. 38- 17967 (1963) discloses an Mo—Bi—Fe—P—O catalyst.

However, use of the conventional types of catalysts in the productions of acrylonitrile results in disadvantages as to, firstly, the reaction must be carried out at a relatively high temperature; secondly, the reaction feed must be in contact with the caytalyst over a long period of time to complete the reaction; and thirdly, a large quantity of by-products is produced from side reactions.

Many attempts have been made to eliminate the above-mentioned disadvantages. As a result of these attempts, several improved types of catalysts have been provided. Such catalysts include an Mo—Bi—Fe—O or an Ni—O catalytic base and three or four additional catalytic elements. These improved catalysts generally produce acrylonitrile in relatively high yield. However, the catalysts have the following disadvantages: firstly, such catalysts are composed of a large number, for example, seven or eight catalytic ingredients and, secondly, the cost of the catalyst is high because the catalysts contain large amounts of expensive bismuth and molybdenum. In addition, a large majority of the above-mentioned catalysts produce a high yield of 70% or more acrylonitrile only when the ammoxidation of propylene is carried out at a temperature of 450° C or higher.

Many types of catalysts contain no bismuth. However, these types of catalysts are disadvantageous because when the reaction is performed to provide a high reaction percentage of propylene, a large majority of the catalysts will show a relatively low selective conversion percentage of propylene into acrylonitrile. Further, these types of catalysts have additional disadvantages in that, firstly, the optimum reaction temperature for the catalyst is relatively high, that is, about 450° C or higher; secondly, the contact time required to complete the reaction is relatively long; and thirdly, the yield of acrylonitrile is relatively low.

In view of the above-mentioned disadvantages, it is clear that producing acrylonitrile with a high yield by using the conventional types of catalysts is quite difficult.

Under these circumstances, it would be desirable to provide a new type of catalyst capable of converting propylene into acrylonitrile at a relatively low reaction temperature of approximately 390° C, during a relatively short period of contact time of about 2 seconds, and with (a) a high yield percentage of about 70% or more of acrylonitrile, (b) a high reaction percentage of propylene, and (c) a high selective conversion of propylene to acrylonitrile. In addition, the new type of catalyst should be able to satisfy the above-mentioned aims without using bismuth, which is very expensive, as an element of the catalyst.

THE INVENTION

As a result of extensive studies to achieve a better, more efficient, and less expensive catalyst, a new type of catalyst has been discovered. This novel catalyst comprises a base catalytic component, consisting of oxides of molybdenum, cobalt, and iron, and a small amount of an additional component which is at least one member selected from the group consisting of oxides of calcium, tungsten, chromium, zirconium, titanium, zinc, manganese and tin, in certain specific ratios. The present invention has been developed on the basis of the above-identified discovery.

Briefly, the methods of the present invention comprise contacting a reaction feed containing an olefin such as propylene, ammonia, and molecular oxygen in the gas phase with a catalyst comprising an oxide composition of the empirical formula:

$$Mo_a Co_b Fe_c X_d O_e$$

wherein X represents at least one atom of an element selected from the group consisting of calcium, tungsten, chromium, zirconium, titanium, zinc, manganese and tin. The subscripts $a$, $b$, $c$, and $d$ respectively denote the number of respective atoms of said elements, the ratio $a:b:c:d$ being in the range of 12: from about 4 to 10: from about 1 to 6: from about 0 to 1.0, and the subscript e denotes the number of oxygen atoms which satisfies the average valence of the elements, the ratio a:e being in the range of 12: from about 40 to 70.

The percentage of selective conversion of propylene into acrylonitrile mentioned above is hereinafter denominated "selectivity percentage of acrylonitrile". It is mathematically defined hereinafter.

The present invention is thus realized by using the novel catalyst disclosed herein. This catalyst exhibits the following marked advantages:

(1) Even when used at a temperature of 390° or lower (which is far lower than the temperature at which the conventional catalytic conversion of propylene into acrylonitrile is industrially carried out), the catalyst show such a high catalystic activity that the conversion reaction can be completed within a contact time of about 2 seconds or less.

(2) Accordingly, the heat necessary to complete the conversion reaction is less than that required in the conventional methods, and the catalyst can be used over a longer period of time than that expended in the conventional methods.

(3) The yield of acrylonitrile per unit quantity of catalyst is higher than that in conventional methods.

(4) The reaction percentage of propylene and the selectivity of conversion to acrylonitrile are higher than those obtained with the conventional methods. Accordingly, lesser amounts of by-products from side reactions and a higher yield of acrylonitrile are produced in the present invention than in the conventional methods.

(5) The cost of the new type of catalyst is lower than that of the conventional catalysts, because the novel catalyst of this invention contains no bismuth.

(6) Accordingly, by using the new type of catalyst, it becomes possible to produce acrylonitrile with a significant commercial advantage.

In the new types of catalyst of the present invention, the atomic ratio of $a:b:c:d$ lies in the range of 12:4 to 10:1 to 6:0 to 1.0. If the quantities of molybdenum, cobalt, and iron are outside the above-specified range, it will become difficult to produce acrylonitrile with a yield of more than 70% at a temperature of about 390° C with a contact time of about 2 seconds. The addition of at least one element from among calcium, tungsten, chromium, zirconium, titanium, zinc, manganese and tin to the Mo—Co—Fe catalytic base results in an increase in the percentage yield of acrylonitrile. It is desirable that the catalyst contain the specified additonal elements in a proportion of 0 to 1.0, and preferably, 0.1 to 0.5, when the proportion of molybdenum in the catalyst is 12.

If the catalyst contains the specified additional elements in an atomic ratio higher than 1.0, both the selectivity percentage of acrylonitrile and the reaction percentage of propylene will decrease. Accordingly, it becomes difficult to produce acrylonitrile with a yield of about 70% or greater.

In the new type of catalyst of the present invention, the elements of the catalytic ingredient exist in the form of oxides thereof. Some of the oxides may form a complex, or plurality of said elements may form a compound together with oxygen.

A wide variety of methods can be used to prepare the catalyst of the present invention. Generally, the catalyst can be prepared by providing an aqueous mixture of a molybdenum-containing compound, a cobalt-containing compound, an iron-containing compound and at least compound containing calcium, tungsten, chromium, zirconium, titanium, zinc, manganese, and/or tin; converting the aqueous mixture into a dried solid mixture; and calcining and dried solid mixture at a temperature of at least 500° C.

The compounds containing the catalyst ingredient elements may be in the forms of oxides, hydroxides, salts, or acids. The salts are preferably capable of being thermally decomposed. The molybdenum-containing compound can be molybdic acid, ammonium molybdate, molybdenum trioxide, phosphomolybdic acid, ammonium phosphomolybdate and/or molybdenum sulfide.

The cobalt-containing compound can be cobalt carbonate, cobalt nitrate, cobalt (II) oxide, cobalt (III) oxide, cobalt chloride, tricobalt tetroxide, cobalt (II) hydroxide, cobalt (III) hydroxide, and/or cobalt sulfide.

The iron-containing compound can be ferrous nitrate, ferric nitrate, ferrous oxide, ferric oxide, ferrous chloride, ferric chloride, ferrous hydroxide, ferric hydroxide, ferric phosphate, iron sulfides, ferrous sulfate and/or ferric sulfate.

The calcium-, tungsen-, chromium-, zirconium-, titanium-, zinc-, manganese-, and tin-containing compounds can be oxides, hydroxides, and/or salts of these elements.

In the preparation of the catalysts, the conversion of the aqueous mixture into the solid mixture can be carried out by evaporation. Alternatively, the aqueous mixture can be subjected to a precipitation treatment wherein all of the catalytic ingredient element-containing compounds are precipitated. The precipitate is readily separated from the mixture by way of filtration, centrifugation, or the like, and then dried.

The solid mixture thus prepared is calcined at a temperature of at least 500° C for a period of time sufficient to convert the solid mixture into an activated catalyst, for example, for at least one hour. The calcining temperature is preferably in its range from 500° to 650° C. A calcining temperature lower than 500° C, will tend to reduce the selectivity percentage of acrylonitrile. A calcining temperature higher than 700° C will tend to decrease the percentage of reaction of the propylene.

The catalyst of the present invention can be composed of the catalytic ingredient alone. However, in order to improve the mechanical strength of the catalyst, it is preferable in certain embodiments that the catalytic ingredient be supported on a carrier. The carrier can consist of any type of conventional carrier material. However, it is preferred that the carrier consist of at least one material selected from the group consisting of silica, alumnia, silica-alumina and silicates. A wide variety of sizes and forms of the catalysts are used. That is, the catalyst of the present invention can be screened to desired size and can be formed into an appropriate form, for example, powder, grains, granules, pellets or tablets having the desired strength, depending upon the purpose and conditions under which the catalyst is to be used. Further, it should be noted that the preparation of the catalyst to obtain the desired form results in no change in the activity of the catalyst.

For the purpose of illustration, procedures for preparing a catalyst of the present invention consisting of molybdenum, cobalt, iron, calcium, tungsten and oxygen will be described below. Predetermined amounts of ammonium molybdate and ammonium tungstate are dissolved in a predetermined amount of hot water.

A predetermined amount of phosphoric acid is added dropwise into the above-prepared solution while simultaneously stirring the solution. An aqueous solution containing predetermined amounts of cobalt nitrate, ferric nitrate and calcium nitrate is added dropwise into the above solution while stirring the mixture. A slurry mixture is thus obtained. The slurry mixture is then evaporated to form a dried solid mixture. The dried solid mixture is calcined at a temperature of at least 500° C, preferably from 500° C to 700° C. In order to prepare a catalytic composition in which the catalyst is borne on a carrier, it is preferred that the carrier be mixed with the above-mentioned slurry mixture. However, it should be understood that the preparation procedures for the catalyst of the present invention are not limited to those of the foregoing illustration.

In the method of the present invention, the reaction feed comprises propylene, ammonia and molecular oxygen. This reaction feed can be prepared by mixing a propylene source in gas phase with ammonia and a molecular oxygen-containing gas. The molecular oxygen-containing gas may be industrially pure oxygen gas. However, it is not required that the molecular oxygen-containing gas have a particularly high concentration of oxygen. Accordingly, the molecular oxygen-containing gas may be air, which is economically advantageous.

It is not mandatory that the propylene source to be used in the method of the present invention be propylene of high purity. However, it is desirable that the propylene source be free from certain types of compounds, for example, from n-butylene and acetylene, which are reactive under the conditions of the catalytic conversion of the propylene.

In a preferred embodiment of the reaction feedstock of the present invention, the molar ratio of propylene to oxygen is in the range of 1:0.8 to 4, and more preferably, 1:1 to 2.5, and the molar ratio of propylene to ammonia is in a range of 1:0.5 to 3.0 and more preferably, 1:0.8 to 1.2.

The reaction feed can contain an inert diluent gas which does not affect the conversion of propylene into acrylonitrile, for example, nitrogen, carbon dioxide and/or steam. Steam is especially effective for increasing not only the selectivity percentage of the desired acrylonitrile but also the durability of the catalytic activity. It is preferable that the proportion by mole of the diluent gas to propylene in the reaction feed be 0.5 or more.

The contact of the reaction feed with the catalyst can be effected under ambient pressure, slightly increased pressure or slightly reduced pressure. However, it is convenient that the contact be effected under ambient pressure.

The reaction in the method of the present invention is carried out at an elevated temperature, preferably, in the range of from 300° to 500° C, and more preferably, from 330° to 450° C. Particularly, the method of the present invention can be effected at the relatively low temperature of about 390° C, because the catalyst of the present invention is highly active at this temperature.

The contact time of the reaction feed with the catalyst can be varied over a wide range. Thus the process of the present invention can be carried out by keeping the reaction feed in contact with the catalyst for 0.3 to 10 seconds, and preferably, 0.5 to 5 seconds, under ambient pressure. However, it should be noted that the catalyst of the present invention makes it possible for the reaction to be completed in a contact time of about 2 seconds.

The catalyst of the present invention can be used in a fluidized bed, a moving bed, or a fixed bed. Especially, the fixed bed is most suitable for the method of the present invention, because the catalytic activity of the catalyst of the present invention can be maintained over a long period of time.

The resultant acrylonitrile from the method of the present invention is isolated from the reaction mixture by any conventional isolation method, for example, the methods disclosed in U.S. Pat. Nos. 3,424,781 and 3,688,002.

By applying the ammoxidation method of the present invention, it becomes possible to produce acrylonitrile with a high yield and an high selectivity percentage of acrylonitrile while restricting the production of undesirable by-products from side reactions. Further, it should be noted that in the method of the present invention, an increase in the reaction percentage of the propylene does not affect the selectivity percentage of acrylonitrile. This is one of the industrial benefits provided by the method of the present invention.

In the Examples, the reaction percentage of propylene, the selectivity percentage of acrylonitrile and the percent yield of acrylonitrile are respectively calculated in accordance with the following equations:

$$\text{Reaction percentage of propylene} = \frac{X_1 - X_2}{X_1} \times 100$$

$$\text{Selectivity percentage of acrylonitrile} = \frac{Y}{X_1 - X_2} \times 100, \text{ and}$$

$$\text{Yield percentage of acrylonitrile} = \frac{Y}{X_1} \times 100$$

wherein $X_1$ denotes the molar amount of propylene contained in the reaction feed prior to the start of the reaction, $X_2$ denotes the molar amount of the residual propylene in the reaction mixture after the completion of the reaction, and Y denotes the molar amount of the acrylonitrile produced.

All parts, percentages, proportions, and ratios herein are by weight, unless otherwise indicated.

The following examples are given to illustrate embodiments of the invention as it is presently preferred to practive it. It will be understood that these examples are illustrative, and the invention is not to be considered as restricted thereto except as indicated in the appended claims.

EXAMPLES 1 THROUGH 5 AND COMPARISON EXAMPLES 1 THROUGH 4

In Example 1, an aqueous slurry of catalytic ingredients is provided as follows: First, 90.0 g of ammonium paramolybdate $[(NH_4)_6 \cdot Mo_7O_{24} \cdot 4H_2O]$ is dissolved in 240 ml of water at 80° C, while stirring the solution. Thereafter, a second solution prepared by dissolving 104.9 g of cobalt nitrate $[Co(NO_3)_2 \cdot 6H_2O]$ and 41.6 g of ferric nitrate $[Fe(NO_3)_3 \cdot 9H_2O]$ in 175 ml of water, is mixed dropwise with the first solution so as to form precipitates. An aqueous slurry mixture is thus obtained.

The slurry mixture is aged overnight and, thereafter, heated on a sand bath until nitrogen oxide and ammonium nitrate cease to be generated, so as to form a dried solid mixture of the above-mentioned materials. The dried solid mixture is admixed with 2% by weight of graphite and formed into tablets, each tablet having a diameter of 5mm and a thickness of 5mm. The tablets are heated to a temperature of 600° C and calcined thereat for 5 hours in a calcining furnace while air is flowed therethrough. The resultant catalyst has an atomic ratio of Mo:Co:Fe of 12:8:4:2.4.

A reaction column is provided by charging 12 ml of the foregoing catalyst into a U-shaped glass tube having an inner diameter of 8 mm. The reaction column is heated to 390° C and maintained at this temperature. A reaction feed prepared by gas phase mixing of propylene, ammonia, air and steam in a mole ratio of 10:11:119:25 is passed through the reaction column at a flow rate of 330 ml/min. The reaction feed is maintained in contact with the catalyst for 2.1 seconds.

In each of Examples 2 through 5, procedures identical to those in Example 1 are carried out, except that the atomic ratios of Mo, Co, and Fe in the catalyst are different, as indicated in Table 1.

In each of Comparison Examples 1 through 4, the same procedures as in Example 1 are repeated, except that the resultant catalyst has an atomic ratio of Mo, Co, and Fe indicated in Table 1. That is, the atomic ratios of Mo, Co, and Fe in the resultant catalysts are outside the range of atomic ratios of these elements in the present invention.

The results of the above-mentioned Examples and Comparison Examples are shown in Table 1.

TABLE 1

| Example No. | Atomic ratio of elements in the catalysts | | | Reaction percentage of propylene | Selectivity percentage of acrylonitrile | Yield percentage of acrylonitrile |
|---|---|---|---|---|---|---|
| | Mo | Co | Fe | | | |
| Example 1 | 12 | 8.4 | 2.4 | 90.2 | 81.0 | 73.1 |
| 2 | 12 | 8.4 | 4.8 | 91.1 | 78.1 | 71.1 |
| 3 | 12 | 8.4 | 1.2 | 90.6 | 79.6 | 72.1 |
| 4 | 12 | 4.2 | 2.4 | 90.1 | 80.2 | 72.3 |
| 5 | 12 | 6.9 | 3.1 | 88.1 | 82.4 | 72.6 |
| Comparison Example 1 | 12 | 1.3 | 2.4 | 97.1 | 55.3 | 53.7 |
| 2 | 12 | 1 | 2.4 | 67.5 | 68.1 | 46.0 |
| 3 | 12 | 8.4 | 0.5 | 75.1 | 40.5 | 30.4 |
| 4 | 12 | 8.4 | 9.0 | 93.6 | 64.9 | 60.7 |

EXAMPLES 6 THROUGH 11 AND COMPARISON EXAMPLE 5

In Example 6, first, 240 ml of water is heated to 80° C, and 90.0 g of ammonium paramolybdate and 2.27 g of ammonium paratungstate [$(NH_4)_{10}W_{12}O_{41} \cdot 5H_2O$] are dissolved in the heated water while stirring. Thereafter, a second solution, prepared by dissolving 104.9 g of cobalt nitrate [$Co(NO_3)_6 \cdot 6H_2O$], 41.6 g of ferric nitrate [$Fe(NO_3)_3 \cdot 9H_2O$] and 2.0 g of calcium nitrate [$Ca(NO_3)_2 \cdot 4H_2O$] in 180 ml of water, is mixed dropwise with the first solution in order to provide an aqueous slurry.

The slurry is treated in the same manner as in Example 1 to prepare a catalyst. The resultant catalyst has the atomic ratio indicated in Table 2.

The same reaction procedures as in Example 1 are carried out using 12 ml of the foregoing Example 6 catalyst.

In each of Examples 7 through 10, the same procedures as those in Example 6 are effected, except that no ammonium paratungstate is used and the resultant catalyst has an atomic ratio of Mo, Co, and Fe as indicated in Table 2 for respective Examples 7 through 10.

In Example 11, procedures identical to those in Example 6 are repeated, except that no calcium nitrate is used. The atomic ratio of Mo, Co, and Fe in the resultant catalyst is the same as in Example 6.

In Comparison Example 5, the same operations as those in Example 8 are repeated except that calcium nitrate is used in an amount such that the resultant catalyst contains calcium in the proportion indicated in Table 2. That is, the proportion (1.2) of calcium is larger than 1.0, the upper limit of the proportion of calcium in the present invention.

The results of Examples 6 through 11 and Comparison Example 5 are shown in Table 2.

TABLE 2

| Example No. | Atomic ratio of elements in the catalysts | | | | | Calcining temperature (° C) | Reaction percentage of propylene | Selectivity percentage of acrylonitrile | Yield percentage of acrylonitrile |
|---|---|---|---|---|---|---|---|---|---|
| | Mo | Co | Fe | Ca | W | | | | |
| Example 6 | 12 | 8.4 | 2.4 | 0.2 | 0.2 | 600 | 93.2 | 82.0 | 76.4 |
| 7 | 12 | 8.4 | 2.4 | 0.1 | — | 600 | 90.5 | 81.0 | 73.3 |
| 8 | 12 | 8.4 | 2.4 | 0.2 | — | 600 | 92.6 | 81.1 | 75.1 |
| 9 | 12 | 8.4 | 2.4 | 0.5 | — | 650 | 92.9 | 80.6 | 74.9 |
| 10 | 12 | 8.4 | 2.4 | 0.8 | — | 600 | 92.5 | 79.6 | 73.6 |
| 11 | 12 | 8.4 | 2.4 | — | 0.2 | 600 | 91.7 | 82.6 | 75.7 |
| Comparison Example 5 | 12 | 8.4 | 2.4 | 1.2 | — | 600 | 95.3 | 62.8 | 59.8 |

EXAMPLES 12 THROUGH 14

In Example 12, a solution is prepared by dissolving 86.5 g of cobalt nitrate [$Co(NO_3)_2 \cdot 6H_2O$], 86.5 g of ferric nitrate [$Fe(NO_3)_3 \cdot 9H_2O$] and 1.70 g of chromium nitrate [$Cr(NO_3)_3 \cdot 9H_2$)] in 500 ml of hot water. Next, 1.13 g of zirconyl nitrate [$ZrO(NO_3)_2 \cdot 2H_2O$] and 90.0 g of ammonium paramolybdate [$(NH_4)Mo_7O_{24} \cdot 4H_2O$] are simultaneously added while stirring the solution in order to provide an aqueous slurry.

The slurry is heated on a sand bath until no further ammonium nitrate ($NH_4NO_3$) is evolved from the mixture, to form a dried solid mixture. The solid mixture is converted into a catalyst in the form of tablets by the same method as in Example 1.

The catalyst is utilized to produce acrylonitrile by the same method as Example 1.

In Example 13, the same operations as those in Example 12 are repeated, except that no chromium nitrate is employed and the resultant catalyst has the atomic ratio of Mo, Co, Fe, and Zr indicated in Table 3.

In Example 14, the same procedures as those in Example 12 are followed, except that no zirconyl nitrate is used and the resultant catalyst has the atomic ratio of Mo, Co, Fe, and Cr indicated in Table 3.

The results of Examples 12 through 14 are set out in Table 3.

TABLE 3

| Example No. | Atomic ratio of elements in the catalysts | | | | | Reaction percentage of propylene | Selectivity percentage of acrylonitrile | Yield percentage of acrylonitrile |
|---|---|---|---|---|---|---|---|---|
| | Mo | Co | Fe | Cr | Zr | | | |
| Example 12 | 12 | 7.0 | 3.1 | 0.1 | 0.1 | 92.4 | 81.7 | 75.5 |
| 13 | 12 | 9.0 | 3.1 | — | 0.2 | 90.4 | 84.8 | 76.7 |
| 14 | 12 | 8.4 | 2.0 | 0.2 | — | 92.5 | 82.0 | 75.9 |

EXAMPLES 15 THROUGH 17

In Example 15, 600 ml of water is heated to 80° C, and 90.0 g of ammonium paramolybdate [$(NH_4)_6Mo_7O_{24} \cdot 4H_2O$] is dissolved in the heated water while stirring. Next, 0.68 g of titanium dioxide, $TiO_2$, is suspended in the solution. Thereafter, 104.9 g of cobalt nitrate [$Co(NO_3)_2 \cdot 6H_2O$], 41.6 g of ferric nitrate [$Fe(NO_3)_3 \cdot 9H_2O$] and 0.63 g of zinc nitrate [$Zn(NO_3)_2 \cdot 6H_2O$] are admixed with the suspension, in order to provide an aqueous slurry.

To prepare a dried solid mixture, the slurry is heated on a sand bath until no ammonium nitrate and nitrogen dioxide are evolved from the mixture. The dried solid mixture is shaped into tablets and calcined at a temperature of 550° C for 10 hours. The resultant catalyst has the atomic ratio of elements indicated in Table 4.

The catalyst is used for producing acrylonitrile by the same method as Example 1.

In Example 16, the same operations as those in Example 15 are repeated, except that no zinc nitrate is used and the resultant catalyst has the atomic ratio of elements indicated in Table 4 for Example 16.

In Example 17, the same procedures as those in Example 15 are repeated, except that no titanium dioxide is used and the resultant catalyst has an atomic ratio of elements indicated in Table 4.

The other results of Examples 15, 16, and 17 are also respectively indicated in Table 4.

through 20 and Comparison Example 6 are indicated in Table 5.

TABLE 5

| Example No. | Atomic ratio of elements in the catalysts | | | | | Calcining temperature (° C) | Reaction percentage of propylene | Selectivity percentage of acrylonitrile | Yield percentage acrylonitrile |
|---|---|---|---|---|---|---|---|---|---|
| | Mo | Co | Fe | Mn | Sn | | | | |
| Example 18 | 12 | 8.4 | 2.4 | 0.2 | 0.2 | 650 | 91.6 | 80.0 | 74.0 |
| 19 | 12 | 8.4 | 2.4 | 0.2 | — | 650 | 92.8 | 81.0 | 75.2 |
| 20 | 12 | 9.0 | 2.0 | — | 0.1 | 650 | 95.9 | 79.1 | 75.9 |
| Comparison Example 6 | 12 | 8.4 | 2.4 | — | 1.2 | 600 | 95.3 | 62.8 | 59.8 |

TABLE 4

| Example No. | Atomic ratio of elements in the catalysts | | | | | Calcining temperature (° C) | Reaction percentage of propylene | Selectivity percentage of acrylonitrile | Yield percentage of acrylonitrile |
|---|---|---|---|---|---|---|---|---|---|
| | Mo | Co | Fe | Ca | Zn | | | | |
| Example 15 | 12 | 8.4 | 2.4 | 0.2 | 0.05 | 550 | 92.9 | 79.0 | 73.4 |
| 16 | 12 | 7.9 | 4.0 | 0.2 | — | 550 | 91.5 | 82.1 | 75.1 |
| 17 | 12 | 8.0 | 3.1 | — | 0.1 | 550 | 96.0 | 78.8 | 75.6 |

EXAMPLES 18 THROUGH 20 AND COMPARISON EXAMPLE 6

In Example 18, 600 ml of water heated to a temperature of 80° C, and 90.0 g of ammonium paramolybdate $[(NH_4)_6Mo_7O_{24}\cdot 4H_2O]$ is dissolved in heated water while stirring. Next, 1.20 g of stannic oxide, $SnO_2$, is suspended in the solution. Thereafter, 104.9 g of cobalt nitrate $[Co(NO_3)_2\cdot 6H_2O]$, 41.6 g of ferric nitrate $[Fe(NO_3)_3\cdot 9H_2O]$ and 2.43 g of manganese nitrate $[Mn(NO_3)_2\cdot 6H_2O]$ are admixed with the suspension, to provide an aqueous slurry.

In order to produce a dried solid mixture, the slurry is heated on a sand bath until no further ammonium nitrate and nitrogen dioxide are evolved from the mixture. The solid mixture is shaped into tablets and calcined at 650° C for 5 hours. The resultant catalyst has the atomic ratio of the elements indicated in Table 5 for Example 18. The catalyst is utilized to produce acrylonitrile by the same method as Example 1.

In Example 19, the same procedures as those in Example 18 are repeated using no stannic oxide.

In Example 20, the same operations as those in Example 18 are repeated, except that no manganese nitrate is employed, and the resultant catalyst has an atomic ratio of the elements as indicated in Table 5.

In Comparison Example 6, the same operations as those in Example 18 are conducted except that no manganese nitrate is used and the resultant catalyst has the atomic ratio of elements indicated in Table 5. That is, the proportion of tin atoms in the catalyst is larger than 1.0, the upper limit of the proportion of tin in the present invention. The remaining results of Examples 18

What is claimed is:

1. A method for the catalytic production of acrylonitrile by ammoxidation of propylene, comprising bringing at an elevated temperature, a reaction feed containing propylene, ammonia and molecular oxygen in the gas phase into contact with a catalyst consisting essentially of an oxide composition according to the formula:

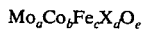

$$Mo_aCo_bFe_cX_dO_e$$

wherein X represents at least one element selected from the group consisting of calcium, tungsten, chromium, zirconium, titanium, zinc, manganese and tin; the subscripts a, b, c, and d respectively represent the atomic ratios a:b:c:d, of the elements in the range of 12:(4 to 10):(1 to 6):(0.1 to 1.0); and the subscript e represents the number of oxygen atoms which satisfies the valence of the elements, the ratio a:e being in the range of 12:40 to 70.

2. A method according to claim 1, wherein contact is effected at a temperature of 300° to 500° C.

3. A method according to claim 2, wherein the contact temperature is in the range of from 330° to 450° C.

4. A method according to claim 3, wherein the contact temperature is approximately 390° C.

5. A method according to claim 1, wherein contact is carried out for 0.3 to 10 seconds.

6. A method according to claim 5, wherein the contact time is in the range from 0.5 to 5 seconds.

7. A method according to claim 6, wherein the contact time is about two seconds.

8. A method according to claim 1, wherein the reaction feed contains an inert diluent gas.

9. A method according to claim 8, wherein the molar proportion of the diluent gas based on the molar amount of propylene in the reaction feed is 0.5 or more.

10. A method according to claim 8, wherein the diluent gas is steam, nitrogen, or carbon dioxide.

11. A method according to claim 1, wherein the source of molecular oxygen is pure oxygen or air.

12. A method according to claim 1, wherein the propylene is substantially free from n-butylene and acetylene.

13. A method according to claim 1, wherein the mole ratio of propylene to oxygen is in the range of 1:1 to 4.

14. A method according to claim 13, wherein the mole ratio of propylene to oxygen is in the range of 1:(1.9 to 2.5)

15. A method according to claim 1, wherein the mole ratio of propylene to ammonia is in the range of 1:(0.5 to 3.0).

16. A method according to claim 15, wherein the mole ratio of propylene to ammonia is in the range of 1:(0.8 to 1.2)

17. A method according to claim 1, wherein the catalyst is carried on a silica, alumina, silica-alumina or silicate support.

18. A method according to claim 1, wherein the catalyst is in a fixed bed, moving bed, or fluidized bed.

* * * * *